United States Patent [19]

Irie et al.

[11] Patent Number: 4,933,349

[45] Date of Patent: Jun. 12, 1990

[54] TREATING AGENT FOR HEART FAILURE

[75] Inventors: Kiyoshi Irie; Satoshi Kunitada; Shinichiro Ashida, all of Tokyo, Japan

[73] Assignee: Daiichi Seiyaku Co., Ltd., Tokyo, Japan

[21] Appl. No.: 212,743

[22] Filed: Jun. 28, 1988

[30] Foreign Application Priority Data

Jul. 1, 1987 [JP] Japan .................. 62-164387

[51] Int. Cl.$^5$ ............... A61K 31/435; A61K 31/425; A61K 31/415

[52] U.S. Cl. .................................. 514/277; 514/365; 514/399; 514/400

[58] Field of Search ............... 514/277, 365, 399, 400

[56] References Cited

U.S. PATENT DOCUMENTS 4,665,188 5/1987 Kanao .................. 546/342

*Primary Examiner*—Frederick E. Waddell
*Attorney, Agent, or Firm*—Sughrue, Mion, Zinn, Macpeak & Seas

[57] ABSTRACT

A preventing and treating agent for heart failure is disclosed, which comprises a compound represented by formula (I):

wherein R represents an imidazolyl group, a thiazolyl group or a pyridyl group; n represents 1 or 2; and m represents an integer of from 1 to 4, or a pharmaceutically acceptable salt thereof as an active ingredient.

1 Claim, No Drawings

TREATING AGENT FOR HEART FAILURE

FIELD OF THE INVENTION

This invention relates to a preventing and treating agent for heart failure which comprises a compound represented by formula (I):

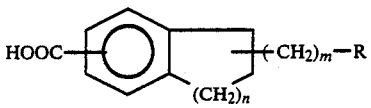

wherein R represents an imidazolyl group, a thiazolyl group or a pyridyl group; n represents 1 or 2; and m represents an integer of from 1 to 4, or a pharmaceutically acceptable salt thereof as an active ingredient.

BACKGROUND OF THE INVENTION

The compounds of formula (I) are known to have therapeutic effects on ischemic heart diseases (U.S. Pat. No. 4,665,188), but unknown for its prophylactic and therapeutic effects on heart, failure.

Generally, the prophylactic and therapeutic effects on ischemic heart diseases cannot be considered to correlate with prophylactic and therapeutic effects on heart failure.

SUMMARY OF THE INVENTION

The inventors have conducted extensive research to find out compounds having prophylactic and treating effects on heart failure. As a result, it has now been found that the compounds represented by formula (I) exhibit the above-described effects, thus reaching the present invention.

This invention relates to a preventing and treating agent for heart failure which comprises a compound represented by formula (I) or a pharmaceutically acceptable salt thereof as an active ingredient.

DETAILED DESCRIPTION OF THE INVENTION

Pharmaceutically acceptable salts of the compound of formula (I) include acid addition salts formed with inorganic acids, e.g., hydrochloric acid, sulfuric acid, nitric acid, etc., or organic acids, e.g., fumaric acid, tartaric acid, maleic acid, succinic acid, oxalic acid, etc.; and salts formed from a carboxyl group and an alkali metal, e.g., sodium, potassium, etc., or an alkaline earth metal, e.g., calcium, magnesium, etc.

Heart failure on which the treating agent of the present invention is effective can be classified by causes, and includes heart failure induced by myocardial infarction, heart failure induced by valvular regurgitation, heart failure induced by pulmonary hypertension, and the like.

The compounds of formula (I) and salts thereof proved highly safe on examination of acute toxicity ($LD_{50}$) in oral administration or intraveneous injection to rats.

The compound of formula (I) or a salt thereof can be formulated into various pharmaceutical preparations, such as tablets, powders, capsules, and injectable solutions, according to known pharmaceutical techniques and is usually administered orally, subcutanesouly, intramuscularly or intravenously.

The dose level of the compound of formula (I) or a salt thereof generally ranges from 50 to 1200 mg/day for adult (body weight: about 50 to 60 kg) in oral administration.

The compound of formula (I) or a salt thereof experimentally exhibited excellent effects in heart failure models, such as an effect to suppress an increase of the diastolic pressure in the left ventricle, an effect to suppress a decrease of the contractile index (dp/dt max/p) or an effect to inhibit cardiac hypertrophy in a model of heart failure induced by myocardial infarction, or an effect to suppress an increase of the systolic pressure in the right ventricle or an effect to inhibit cardiac hypertrophy in a model of heat failure induced by pulmonary hypertension. Therefore, the compound of formula (I) or a salt thereof is useful as a preventing and treating agent for heart failure.

The present invention is now illustrated in greater detail with reference to the following Test Examples and Reference Example, but it should be understood that the present invention is not limited thereto.

TEST EXAMPLE 1

Efficacy in Heart Failure induced by Myocardial Infarction

Test Animal:

SD-SLC male rats (body weight: 272 to 315 g) (purchased from Shizuoka Jikken Dobutsu Kyodo Kumiai) were used as test animals. Intercostal thoracotomy was made on the left chest of the rat anesthesized with pentobarbital (50 mg/kg, i.p.). The left coronary artery was then ligated at the position 2 to 3 mm away from its origin according to the method of Selye et al, *Angiology*, Vol. 11, 398 (1960). Immediately after confirming that the peripheral cardiac muscle of the open chest rat was involved in ischemia, the opening was closed, and the animal was fed on food and tap water ad lib.

As a sham operation group, another group of rats received thoracotomy in the same manner as described above except for carrying out no ligation of the coronary artery.

Administration of Drug:

6-(1-Imidazolylmethyl)-5,6,7,8-tetrahydronaphthalene-2-carboxylic acid hydrochloride hemihydrate (herein-after referred to as Compound A) was dissolved in ion-exchanged water and orally administered to the test animals at a single daily doze of 10 mg/5 ml/kg 6 times per week for consecutive 1 month from 5 hours after the ligation of the coronary artery. A control group orally received 5 ml/kg/day of ion-exchanged water only.

Measurements:

On the next day of the final administration of Compound A, a catheter was inserted into the femoral artery and the left ventricle of the rat under anesthesia with Inactin (100 mg/kg, i.p.), and systemic mean blood pressure, maximum rate of increase of the intraventricular pressure (LV dp/dt max), contractile index (LV dp/dt max/p), left ventricular systolic pressure, left ventricular diastolic pressure and heart rate were measured. The results expressed as means±S.E. were shown in Table 1 below.

After completion of these measurements, the heart was excised and divided into the left ventricle (including the septum) and the right ventricle. The wet weight of each ventricle was measured. The results expressed as mean±S.E. were shown in Table 2 below.

Test Results:

TABLE 1

Efficacy in A Model of Heart Failure induced by Myocardial Infraction

| Measurement Item | Sham Operation Group (n = 7) | Control Group (n = 5) | Test Group (n = 7) |
|---|---|---|---|
| Mean Blood Pressure (mmHg) | 148 ± 7 | 128 ± 5 | 132 ± 5 |
| Left Ventricular Systolic Pressure (mmHg) | 162 ± 6 | 139 ± 5* | 143 ± 6* |
| Heart Rate (/min) | 426 ± 8 | 139 ± 18* | 399 ± 14 |
| Maximum Increasing Rate of Left Intra-ventricular Pressure (LV dp/dt max, mmHg/sec) | 8188 ± 322 | 5436 ± 384** | 6356 ± 4780** |
| Contractile Index (LV dp/dt max/p. /sec) | 100 ± 3 | 64 ± 3** | 79 ± 5**# |
| Left Ventricular Diastolic Pressure (cmH$_2$O) | 0.2 ± 0.5 | 21.0 ± 1.6** | 12.0 ± 3.2**# |

Note:
n = Number of test animals.
*P < 0.05,
**P < 0.01 (as compared with the sham operation group)
P < 0.05 (as compared with the control group)

As is apparent from Table 1, in the animals whose coronary artery was ligated (control group), left ventricular systolic pressure, heart rate, increasing rate of left intraventricular pressure and contractile index decreased, and left ventricular diastolic pressure increased remarkably as compared with the animals having received a sham operation (sham operation group). These changes in the items indicated that the animals of control group suffered from heart failure. On the other hand, in the animals with the coronary artery ligation and having been administered with Compound A for 1 month (test group), the inhibition on reduction of contractile index and on elevation of left ventricular diastolic pressure was observed.

TABLE 2

Efficacy on Cardiac Hypertrophy in a Model of Heart Failure induced by Myocardial Infarction

| Weight of Ventricle (g) | Sham Operation Group (n = 7) | Control Group (n = 5) | Test Group (n = 7) |
|---|---|---|---|
| Left | 0.876 ± 0.051 | 0.985 ± 0.040 | 0.861 ± 0.029* |
| Right | 0.238 ± 0.011* | 0.439 ± 0.044 | 0.361 ± 0.028 |
| Total | 1.115 ± 0.060** | 1.424 ± 0.076 | 1.222 ± 0.052* |

Note:
*P < 0.05,
**P < 0.01 (as compared with the control group).

As shown in Table 2, in the animals with their coronary artery ligation (control group) an increase of the ventricules in weight or a tendency thereto as compared with the sham operation group was observed. Whereas, such an increase of the ventricle weight can be suppressed significantly in the test group administered with Compound A.

As demonstrated above, the long-term administration of Compound A improved reduction of cardiac contractility and relieved pressure load to the heart to inhibit cardiac hypertrophy without adversely affecting the blood pressure in animals suffering from heart failure induced by myocardial infarction. Therefore, Compound A proved useful for prevention and treatment of heart failure.

TEST EXAMPLE 2

Efficacy in Monocrotaline-Induced Heart Failure Model (A Model of Heart Failure induced by Pulmonary Hypertension)

Test Animal:

SD-SLC male rats (body weight: 160 to 190 g) were used. Monocrotaline was dissolved in 1N hydrochloric acid, and the solution was adjusted to a pH of 7.4 with a 1N sodium hydroxide aqueous solution. Distilled water was added thereto to make a 40 mg/ml solution. The solution was subcutaneously administered to the rats at a dose of 40 mg/kg to prepare right ventricular insufficient rats.

Another group of rats was subcutaneously administered with 1 ml/kg of physiological saline only and served as intact control.

Administration of Drug:

Compound A was dissolved in distilled water. Six hours from the administration of Monocrotaline, the solution was orally administered to the test animals at a single daily dose of 10 mg/kg for consecutive 1 month (6 days per week). As a control group, the right ventricular insufficient rats orally received 5 ml/kg of distilled water only.

Measurement:

On the next day of the final administration of Compound A, a catheter was inserted into the right ventricle under anesthesia with pentobarbital (50 mg/kg, i.p.), and the right ventricular systolic pressure was measured. Thereafter, the heart was excised, divided into the left ventricle (including the septum) and the right ventricle, and the wet weight of each ventricle was determined. The results obtained are given in Table 3, as expressed as mean±S.E.

TABLE 3

| Measurement Item | Intact Control Group (n = 5) | Control Group (n = 12) | Test Group (N = 7) |
|---|---|---|---|
| Right Ventricular Systolic Pressure (mmHg) | 33.7 ± 0.6 | 67.3 ± 5.2* | 46.9 ± 4.9*# |
| Right Ventricle Weight/Left Ventricle Weight | 0.26 ± 0.01 | 0.50 ± 0.03** | 0.41 ± 0.04** |

Note:
*P < 0.05,
**P < 0.01 (as compared with the intact control group)
P < 0.05 (as compared with the control group)

As is apparent from Table 3, in the Monocrotaline treated group (control group) the right ventricular systolic pressure and the right ventricular hypertrophy increased conspicuously after 1 month from the administration of Monocrotaline, indicating heart failure conditions. However, it was seen that the administration of Compound A to the animals suffering from Monocrotaline-induced heart failure for 1 month significantly inhibited the increase in the right ventricular systolic pressure and showed a tendency to inhibit the right ventricular hypertrophy.

Thus, long-term administration of Compound A exhibited improvements of heart failure induced by pulmonary hypertension. Therefore, Compound A proved useful for the prevention and treatment of heart failure.

TEST EXAMPLE 3

Acute toxicities of Compound A in rats through oral administration or intravenous injection were as follows.

TABLE 4

Acute Toxicity in Rats

| $LD_{50}$ (mg) | | |
|---|---|---|
| Male | Female | |
| 2438 | 1994 | (p.o.) |
| 807 | 783 | (i.v.) |

REFERENCE EXAMPLE

| | |
|---|---|
| Compound A | 20 mg |
| Lactose | 50 mg |
| Corn Starch | 25.5 mg |
| Hydroxypropyl Cellulose | 4 mg |
| Magnesium Stearate | 0.5 mg |

TABLE 4-continued

Acute Toxicity in Rats

Total 100 mg per one tablet

According to the above formulation, the tablet containing Compound A was prepared by a usual pharmaceutical technique for the preparation of tablets.

While the invention has been described in detail and with reference to specific embodiments thereof, it will be apparent to one skilled in the art that various changes and modifications can be made therein without departing from the spirit and scope thereof.

What is claimed is:

1. A method for therapeutic treatment of heart failure which comprises administering to a patient in need of therapeutic treatment for heart failure an amount of a compound represented by formula (I) or a pharmaceutically acceptable salt thereof effective for therapeutic treatment of heart failure

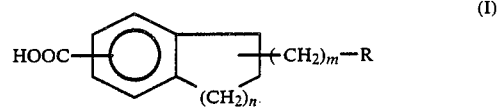
(I)

wherein R represents an imidazolyl group, a thiazolyl group or a pyridyl group; n represents 1 or 2; and m represents an integer of from 1 to 4.

* * * * *